United States Patent
Lin et al.

(10) Patent No.: US 9,339,028 B2
(45) Date of Patent: May 17, 2016

(54) METHOD FOR INHIBITING MICROORGANISMS OR PLANT PESTS USING EXFOLIATED CLAY/SURFACTANT COMPLEX

(71) Applicant: NATIONAL TAIWAN UNIVERSITY, Taipei (TW)

(72) Inventors: Jiang-Jen Lin, Taipei (TW); Ying-Chiao Wang, Taipei (TW); Pei-Ru Li, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 360 days.

(21) Appl. No.: 13/933,913

(22) Filed: Jul. 2, 2013

(65) Prior Publication Data

US 2013/0296270 A1   Nov. 7, 2013

Related U.S. Application Data

(63) Continuation of application No. 13/007,906, filed on Jan. 17, 2011, now abandoned.

(30) Foreign Application Priority Data

Jun. 4, 2010   (TW) ................ 99118254 A

(51) Int. Cl.
```
A01N 25/04    (2006.01)
A01N 25/30    (2006.01)
A01N 33/12    (2006.01)
A01N 31/02    (2006.01)
A01N 25/34    (2006.01)
A01N 59/00    (2006.01)
A01N 61/00    (2006.01)
A01N 55/02    (2006.01)
```
(52) U.S. Cl.
CPC ............... *A01N 25/04* (2013.01); *A01N 25/30* (2013.01); *A01N 25/34* (2013.01); *A01N 31/02* (2013.01); *A01N 33/12* (2013.01); *A01N 55/02* (2013.01); *A01N 59/00* (2013.01); *A01N 61/00* (2013.01)

(58) Field of Classification Search
CPC ....... A01N 25/04; A01N 25/30; A01N 31/02; A01N 33/12; A01N 55/02; A01N 59/00
See application file for complete search history.

(56) References Cited

U.S. PATENT DOCUMENTS

| | | | |
|---|---|---|---|
| 4,929,644 A * | 5/1990 | Guilbeaux | A01N 25/08 514/642 |
| 7,022,299 B2 | 4/2006 | Lin et al. | |
| 7,094,815 B2 | 8/2006 | Lin et al. | |
| 7,125,916 B2 | 10/2006 | Lin et al. | |
| 2005/0239943 A1 | 10/2005 | Lin et al. | |
| 2006/0287413 A1 | 12/2006 | Lin et al. | |
| 2007/0224293 A1 * | 9/2007 | Hughes | A01N 59/00 424/683 |
| 2009/0146107 A1 * | 6/2009 | Lin | B01F 17/005 252/363.5 |
| 2009/0148484 A1 * | 6/2009 | Lin | A01N 59/16 424/409 |

OTHER PUBLICATIONS

Hsu, S.H., et al.; ACS Applied Materials & Interfaces, 2009, p. 2556-2564.*

* cited by examiner

*Primary Examiner* — Robert Jones, Jr.
(74) *Attorney, Agent, or Firm* — Pai Patent & Trademark Law Firm; Chao-Chang David Pai

(57) ABSTRACT

The present invention provides a method for inhibiting microorganisms or plant pests using exfoliated clay/surfactant complex. The weight ratio of the exfoliated clay to the surfactant can range from 99/1 to 1/99. Preferably, the exfoliated clay is an inorganic layered clay on a nano scale and the surfactant is cationic, nonionic, anionic or amphoteric.

4 Claims, 2 Drawing Sheets

METHOD FOR INHIBITING MICROORGANISMS OR PLANT PESTS USING EXFOLIATED CLAY/SURFACTANT COMPLEX

CROSS REFERENCE TO RELATED APPLICATIONS

The present application is a continuation of prior U.S. application Ser. No. 13/007,906 filed Jan. 17, 2011, entitled "EXFOLIATED CLAY/SURFACTANT COMPLEX FOR INHIBITING MICROORGANISMS, VIRUSES OR PLANT PESTS". The prior U.S. Application claims priority of Taiwan Patent Application No. 099118254, filed on Jun. 4, 2010, the entirety of which is incorporated herein by reference.

BACKGROUND OF THE INVENTION

1. Field of the Invention

The present invention relates to a method for inhibiting microorganisms or plant pests using exfoliated clay/surfactant complex. Therefore, the present invention is suitable for fields including agriculture, fisheries and soil remediation.

2. Related Prior Arts

Most of drugs or materials for inhibiting microorganisms or viruses, for example, pesticides sprayed on growing plants or preservatives applied to agricultural and livestock products, are not only toxic to human bodies but also ruinous to the environment.

In order to inhibit growth of microorganisms and viruses, proper materials having smaller volume than them (for example, on a nano scale) can be used. Nanosilicate platelets (NSPs) achieved by exfoliating clay are also considered due to their high aspect ratio (averagely, 100×100×1 nm3), high surface areas (700 to 800 m²/g) and strong charges (ca. 20,000 ions per platelet). However, because of these special characteristics, nanosilicate platelets have different electrical properties at different pH values. Below the isoelectric point (IEP=pH 6.4), surfaces of the NSPs are electrically positive and aggregation will occur. That is, the NSPs are not suitable to be used alone as effects thereof could be influenced by pH values.

Accordingly, the present invention provides a method of applying NSPs to inhibiting microorganisms, viruses or plant pests without aggregation.

SUMMARY OF THE INVENTION

The object of the present invention is to provide an exfoliated clay/surfactant complex which can effectively inhibit growth of microorganisms, viruses or plant pests without self-aggregation.

For the exfoliated clay/surfactant complex of the present invention, the weight ratio of the exfoliated clay to surfactant ranges from 99/1 to 1/99, preferably from 99/1 to 50/50, and more preferably from 99/1 to 90/10. The exfoliated clay is preferably inorganic layered clay on the nano scale; and more preferably nanosilicate platelets (NSPs). The surfactant can be a cationic surfactant, nonionic surfactant, anionic surfactant or amphoteric surfactant; preferably the surfactant is a cationic, nonionic surfactant or anionic surfactant; and more preferably a cationic surfactant. The cationic surfactant can be a quaternary ammonium salt of a fatty amine having 12 to 32 carbon atoms or a quaternary ammonium chloride of a fatty amine having 12 to 32 carbon atoms. The nonionic surfactant can be octylphenol polyethoxylate or polyoxyethylene alkyl ether.

Preferably, the cationic surfactant is ammonium chloride of tallow having 12 to 18 carbon atoms or ammonium chloride of hydrogenated tallow, quaternary ammonium salt of octadecyl fatty amine, octadecyl ammonium chloride or alkyl dimethyl benzyl ammonium chloride; and more preferably alkyl dimethyl benzyl ammonium chloride.

Preferably, the nonionic surfactant is polyoxyethylene alkyl ether, polyoxyethylene stearylcetyl ether, sorbitan esters of fatty acids (for example, Span® series of MERCK), Polysorbate (for example, Tween® series of MERCK), alkylphenol ethoxylates, nonylphenol ethoxylates (NPEOs), or fatty alcohol ethoxylates.

The surfactant suitable for the present invention is exemplified as follows, which shows good effects of inhibiting bacteria or plant pests.

Hybrid Surfactants of Exfoliated Silicate Platelets and Surfactants

NSP/$C_{18}H_{37}NH_3^+Cl^-$
[Octadecylamine]

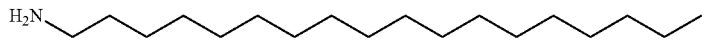 [SMILES: CCCCCCCCCCCCCCCCCCN]

NSP/ABLUMINE 1214
[Alkyl($C_{12}$:$C_{14}$:$C_{16}$ = 63:30:7)
Dimethyl Benzyl Ammonium Chloride]

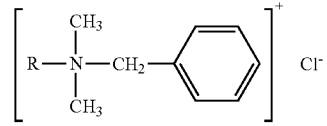

NSP/ABLUMINE TMC
[Cetyl Trimethyl Ammonium Chloride]

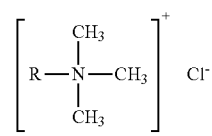

NSP/ABLUMINE DD
[Didecyl Dimethyl Ammonium Chloride]

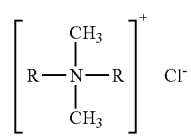

| Hybrid Surfactants of Exfoliated Silicate Platelets and Surfactants |  |
|---|---|
| NSP/ABLUMINE M462<br>[Alkyl($C_{32}$) Trimethyl Ammonium Chloride] | $\left[ R-\underset{\underset{CH_3}{\mid}}{\overset{\overset{CH_3}{\mid}}{N}}-CH_3 \right]^+ Cl^-$ |
| NSP/ABLUMINE DHT75<br>[Dihydrogenated Tallow<br>Dimethyl Ammonium Chloride] | $\left[ R-\underset{\underset{CH_3}{\mid}}{\overset{\overset{CH_3}{\mid}}{N}}-H \right]^+ Cl^-$ |
| NSP/Triton X-100<br>[Triton X-100] | $C_8H_{17}-\langle\bigcirc\rangle-(OCH_2CH_2)_{\overline{9.5}}-OH$ |
| NSP/SDS<br>[Sodium dodecyl sulfate] | $CH_3-(CH_2)_{\overline{11}}-O-\underset{\underset{O}{\parallel}}{\overset{\overset{O}{\parallel}}{S}}-O^- \ Na^+$ |
| NSP/SINOPOL 1816<br>$C_{18}H_{37}O-(CH_2CH_2O)_{\overline{16}}-H$ |  |
| NSP/SINOPOL 1830<br>$C_{18}H_{37}O-(CH_2CH_2O)_{\overline{30}}-H$ |  |
| NSP/SINOPOL 2307<br>$C_{13}H_{27}O-(CH_2CH_2O)_{\overline{7}}-H$ |  |
| NSP/SINOPOL 2340<br>$C_{13}H_{27}O-(CH_2CH_2O)_{\overline{40}}-H$ |  |

The method for producing the exfoliated clay/surfactant complex of the present invention is: mix the exfoliated clay and the surfactant in a solvent for complexing.

The exfoliated clay and the surfactant are preferably respectively dissolved in the solvent and then mixed. The solvent is preferably water.

The exfoliated clay/surfactant complex of the present invention can be dissolved in a solvent and then mixed with plants, for example, spraying on plants or soil, or mixing in water. The complex can be in water to form a solution having a concentration of about 0.01 to 1 wt %.

DETAILED DESCRIPTION OF THE PREFERRED EMBODIMENTS

Figure 1:
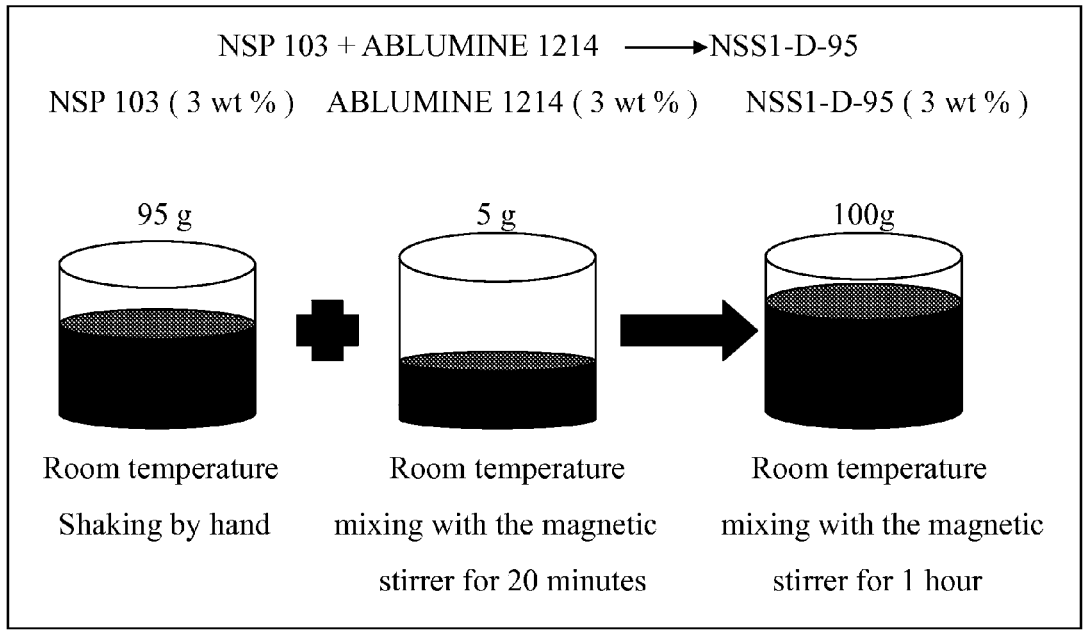
FIG. 1 shows the procedure of Example 1.

The materials used in the present invention include:
1. Ablumine 1214: Alkyl dimethyl benzyl ammonium chloride, a kind of ammonium chloride of tallow having 12 to 18 carbon atoms or ammonium chloride of hydrogenated tallow, a cationic surfactant, purchased from Taiwan Surfactant Co.
2. SINOPOL 1830: Polyoxyethylene stearylcetyl ether, a kind of polyoxyethylene alkyl ether, a nonionic surfactant, purchased from SINO-JAPAN CHEMICAL.
3. SDS: Sodium dodecyl sulfate, an anionic surfactant.
4. Nanosilicate platelets (NSPs): Referring to the following description or U.S. Pat. Nos. 7,022,299 B2, 7,094,815 B2, or 7,125,916 B2, Pub. No. 2005-0239943-A1, or Ser. No. 11/464,495.

[Preparing Nanosilicate Platelets (NSPs)]

Step (a): Sodium montmorillonite ($Na^+$-MMT) (10 g, 11.5 meq, purchased from Nanocor Ind. Co.) is previously dispersed in water (1 L, 80° C.) in a beaker and swelled by vigorously stirring for 4 hours to form an earth-colored uniform dispersion.

Step (b): In a reactor, p-cresol (27.2 g) and poly(propylene glycol)-diamine (Jeffamine D-2000, 757.6 g) are dissolved in toluene (200 ml) and the mixture is heated to 90° C. for 3 hours. Formaldehyde (37 wt %, 61.4 g) is then added and the temperature is raised to 130° C. After stirring continuously for five hours, a viscous product, amine-termination Mannich oligomer (AMO), is obtained. The gel permeation chromatography (GPC) analysis shows three major peaks at Mw 3,100, Mw 6,200 and Mw 9,200. Titration for amine of the AMO indicates 0.4 meq/g for primary amine, 0.56 meq/g for secondary amine, and zero for tertiary amine. Then the AMO (57.5 g) is dissolved in water and mixed with concentrated hydrochloric acid (35 wt %, 36 g) at 80° C. for 30 minutes to acidify the AMO. The acidified AMO is then added into the $Na^+$-MMT dispersion of Step (a). After the mixture is stirred for five hours, a solution of AMO/Clay is prepared.

Step (c): Buffer solutions with different pH values are added into the solution of AMO/Clay, which then becomes cream color and viscous.

Step (d): To the viscous solution, ethanol (7.5 L) is added and filtered. The precipitate is then mixed with ethanol (10 L) and NaOH (9.2 g). The mixture is then filtered to obtain a cream-color, semi-opaque mixture of AMO/Clay which has an organic-to-inorganic ratio of about 40/60.

Step (e): the above mixture of AMO/Clay is added into ethanol (10 L) and NaOH. Water (10 L) and toluene (10 L) are then sequentially added and mixed well with the mixture. After one day, the mixture is divided into three layers wherein the upper layer is toluene containing the AMO, the middle layer is ethanol, and the lower layer is water containing nanosilicate platelets (referred to as NSP103S).

The natural or synthetic clay suitable for preparing the NSPs also includes:
a. Bentonite: synthetic layered silicate clay, for example, SWN of CO—OP Chemical Co. which has a cationic exchange capacity (CEC) of 0.67 mequiv/g.
b. Synthetic fluorine mica, for example, SOMASIF ME-100 of CO—OP Chemical Co. which has a CEC of 1.20 mequiv/g.
c. Laponite: synthetic layered silicate clay having a CEC of 0.69 mequiv/g.
d. $[M^{II}_{1-x}M^{III}_x(OH)_2]_{intra}[A^{n-}.nH_2O]_{inter}$: synthetic layered silicate clay, wherein $M^{II}$ indicates the two-valent metal ion, for example, Mg, Ni, Cu, or Zn; $M^{III}$ indicates the three-valent metal ion, for example, Al, Cr, Fe, V, or Ga; $A^{n-}$ indicates the anion, for example, $CO_3^{2-}$, $NO_3^-$; the anions have an anionic exchange capacity (AEC) from 2.00 to 4.00 mequiv/g.

The Examples described below show the preferred embodiments of the present invention, which illustrate, but not limit, the scope of the present invention.

EXAMPLE 1

Step (A): To a beaker, NSP103S (9.7 wt %, 0.31 g) and deionic water (89.69 g) are added and the beaker is shaken at room temperature to prepare a solution of NSP 103 (0.033 wt %).
Step (B): To another beaker, Ablumine 1214 (50 wt %, 5.94 g) and deionic water (4.06 g) are added and mixed with a magnetic stirrer at room temperature for 20 minutes to prepare a solution of Ablumine 1214 (29.7 wt %).
Step (C): The solutions of Step (A) and Step (B) are then mixed at room temperature for one hour and a composite of NSP/Ablumine 1214 having a weight ratio of 1/99 is obtained (referred to as NSS1-D-01) (3 wt %).

EXAMPLE 2

Step (A): To a beaker, NSP103S (9.7 wt %, 29.4 g) and deionic water (60.6 g) are added and the beaker is shaken at room temperature to prepare a solution of NSP 103 (3.2 wt %).
Step (B): To another beaker, Ablumine 1214 (50 wt %, 0.3 g) and deionic water (9.7 g) are added and mixed with a magnetic stirrer at room temperature for 20 minutes to prepare a solution of Ablumine 1214 (1.5 wt %).
Step (C): The solutions of Step (A) and Step (B) are then mixed at room temperature for one hour and a composite of NSP/Ablumine 1214 having a weight ratio of 95/5 is obtained (referred to as NSS1-D-95) (3 wt %). The procedure is shown in FIG. 1.

EXAMPLE 3

Step (A): To a beaker, NSP103S (9.7 wt %, 30.6 g) and deionic water (59.4 g) are added and the beaker is shaken at room temperature to prepare a solution of NSP 103 (3.3 wt %).
Step (B): To another beaker, Ablumine 1214 (50 wt %, 0.06 g) and deionic water (9.94 g) are added and mixed with a magnetic stirrer at room temperature for 20 minutes to prepare a solution of Ablumine 1214 (0.3 wt %).
Step (C): The solutions of Step (A) and Step (B) are then mixed at room temperature for one hour and a composite of NSP/Ablumine 1214 having a weight ratio of 99/1 is obtained (referred to as NSS1-D-99) (3 wt %).

EXAMPLE 4

Step (A): To a beaker, NSP103S (9.7 wt %, 0.31 g) and deionic water (89.69 g) are added and the beaker is shaken at room temperature to prepare a solution of NSP 103 (0.033 wt %).
Step (B): To another beaker, SINOPOL 1830 (100 wt %, 2.97 g) and deionic water (7.03 g) are added and mixed with a magnetic stirrer at room temperature for 20 minutes to prepare a solution of SINOPOL 1830 (29.7 wt %).
Step (C): The solutions of Step (A) and Step (B) are then mixed at room temperature for one hour and a composite of NSP/SINOPOL 1830 having a weight ratio of 1/99 is obtained (referred to as NSS2-D-01) (3 wt %).

EXAMPLE 5

Figure 2:
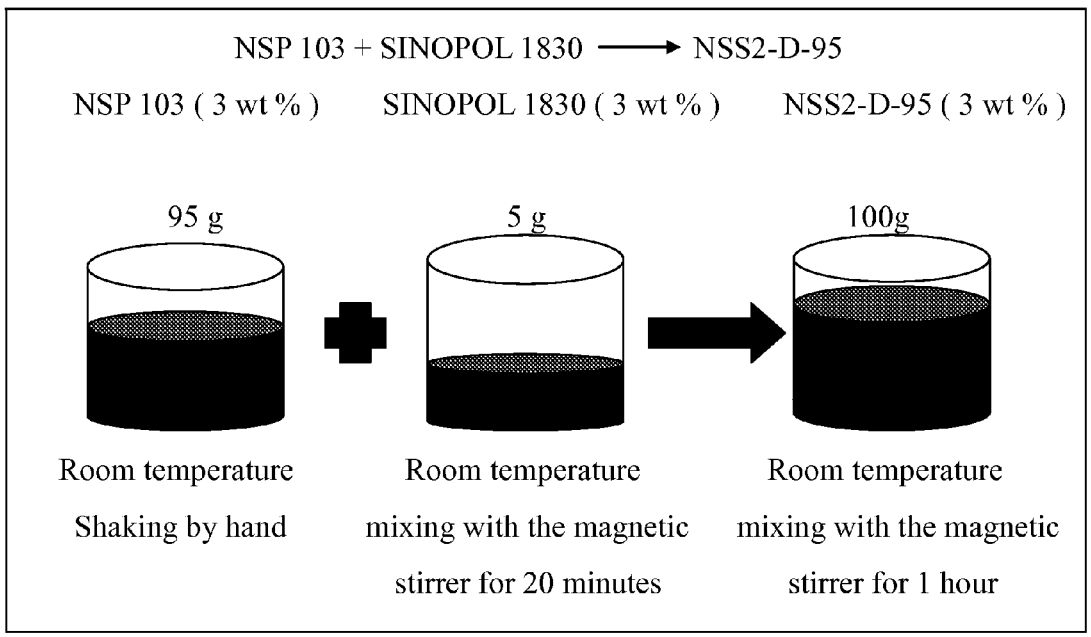
FIG. 2 shows the procedure of Example 5.

Step (A): To a beaker, NSP103S (9.7 wt %, 29.4 g) and deionic water (60.6 g) are added and the beaker is shaken at room temperature to prepare a solution of NSP 103 (3.2 wt %)
Step (B): To another beaker, SINOPOL 1830 (100 wt %, 0.15 g) and deionic water (9.85 g) are added and mixed with a magnetic stirrer at room temperature for 20 minutes to prepare a solution of SINOPOL 1830 (1.5 wt %).
Step (C): The solutions of Step (A) and Step (B) are then mixed at room temperature for one hour and a composite of NSP/SINOPOL 1830 having a weight ratio of 95/5 is obtained (referred to as NSS2-D-95) (3 wt %). The procedure is shown in FIG. 2.

EXAMPLE 6

Step (A): To a beaker, NSP103S (9.7 wt %, 30.6 g) and deionic water (59.4 g) are added and the beaker is shaken at room temperature to prepare a solution of NSP 103 (3.3 wt %)
Step (B): To another beaker, SINOPOL 1830 (100 wt %, 0.03 g) and deionic water (9.97 g) are added and mixed with a magnetic stirrer at room temperature for 20 minutes to prepare a solution of SINOPOL 1830 (0.3 wt %).
Step (C): The solutions of Step (A) and Step (B) are then mixed at room temperature for one hour and a composite of NSP/SINOPOL 1830 having a weight ratio of 99/1 is obtained (referred to as NSS2-D-99) (3 wt %).

EXAMPLE 7

Step (A): To a beaker, NSP103S (9.7 wt %, 0.31 g) and deionic water (89.69 g) are added and the beaker is shaken at room temperature to prepare a solution of NSP 103 (0.033 wt %).
Step (B): To another beaker, SDS (100 wt %, 2.97 g) and deionic water (7.03 g) are added and mixed with a magnetic stirrer at room temperature for 20 minutes to prepare a solution of SDS (29.7 wt %).
Step (C): The solutions of Step (A) and Step (B) are then mixed at room temperature for one hour and a composite of NSP/SINOPOL 1830 having a weight ratio of 1/99 is obtained (referred to as NSS3-A-01) (3 wt %).

EXAMPLE 8

Step (A): To a beaker, NSP103S (9.7 wt %, 29.4 g) and deionic water (60.6 g) are added and the beaker is shaken at room temperature to prepare a solution of NSP 103 (3.2 wt %).
Step (B): To another beaker, SDS (100 wt %, 0.15 g) and deionic water (9.85 g) are added and mixed with a magnetic stirrer at room temperature for 20 minutes to prepare a solution of SDS (1.5 wt %).
Step (C): The solutions of Step (A) and Step (B) are then mixed at room temperature for one hour and a composite of NSP/SDS having a weight ratio of 95/5 is obtained (referred to as NSS3-A-95) (3 wt %).

EXAMPLE 9

Step (A): To a beaker, NSP103S (9.7 wt %, 30.6 g) and deionic water (59.4 g) are added and the beaker is shaken at room temperature to prepare a solution of NSP 103 (3.3 wt %).
Step (B): To another beaker, SDS (100 wt %, 0.03 g) and deionic water (9.97 g) are added and mixed with a magnetic stirrer at room temperature for 20 minutes to prepare a solution of SDS (0.3 wt %).
Step (C): The solutions of Step (A) and Step (B) are then mixed at room temperature for one hour and a composite of NSP/SDS having a weight ratio of 99/1 is obtained (referred to as NSS3-A-99) (3 wt %).

The surfactants and the NSP/surfactant weight ratios of the above Examples are shown in Table 1.

TABLE 1

| Examples | Surfactants | NSP/Surfactant (w/w) | Product |
|---|---|---|---|
| 1 | Ablumine 1214 | 1/99 | NSS1-D-01 |
| 2 | (cationic) | 95/5 | NSS1-D-95 |
| 3 | | 99/1 | NSS1-D-99 |
| 4 | SINOPOL 1830 | 1/99 | NSS2-D-01 |
| 5 | (nonionic) | 95/5 | NSS2-D-95 |
| 6 | | 99/1 | NSS2-D-99 |
| 7 | SDS | 1/99 | NSS3-A-01 |
| 8 | (anionic) | 95/5 | NSS3-A-95 |
| 9 | | 99/1 | NSS3-A-99 |

In Step (A) and Step (B), the NSPs and the surfactant are preferably diluted to the same concentration so that the effect of modifying NSPs is better.

[Tests for Inhibiting Growth of Bacteria]
1. Selecting *Escherichia coli*.
2. Preparing the standard solution of bacteria.

The solution of bacteria incubated overnight is added into a liquid medium of fresh Luria-Bertani (LB) and is continuously incubated for three hours. The volumetric ratio of the solution of bacteria to the liquid medium is 1/100. Absorbance of the incubated solution at $OD_{600}$ is measured with a spectrophotometer and the solution having $OD_{600}$ ranging from 0.4 to 0.6 is selected for the standard solution.

Figure 3:
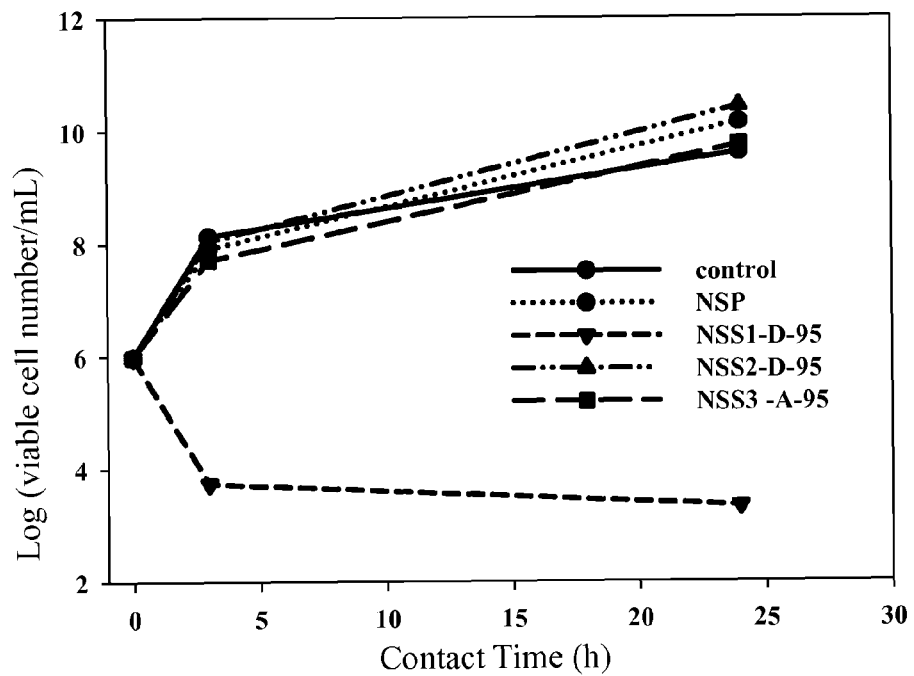
FIG. 3 shows the effects of the NSPs/surfactant complexes of Examples 2, 5 and 8 in inhibiting growth of bacteria.

FIG. 3 shows the effects of the NSPs/surfactant complexes of Examples 2, 5 and 8 in inhibiting growth of bacteria. The NSPs/surfactant complexes have a weight ratio of 99/5 and a concentration 0.1 wt %. The results indicate that the complex (NSS 1-D-95) of Example 2 including the cationic surfactant performs the best effect when the bacteria are electrically negative.

Figure 4:
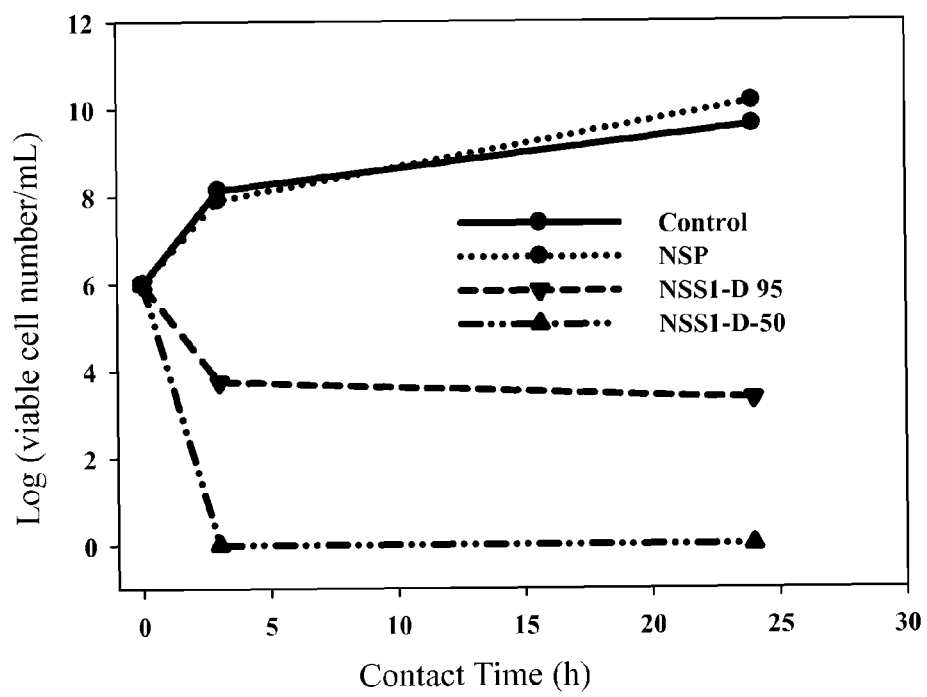
FIG. 4 shows the effects of the NSPs/surfactant complexes with different weight ratios in inhibiting growth of bacteria.

FIG. 4 shows the effects of the NSPs/surfactant complexes with different weight ratios in inhibiting growth of bacteria. The results indicate that the NSPs/surfactant complexes with a weight ratio 50/50 (prepared from Examples 2 and 3, NSS1-D-50) perform better effects than that with a weight ratio 95/5 (Example 2, NSS1-D-95), in a concentration of 0.1 wt %. That is, more cationic surfactant facilitates inhibiting growth of bacteria.

[Tests for Inhibiting Plant Pests]

The NSPs/nonionic surfactant complexes of Examples 4 to 6 are respectively mixed with alcohol in a weight ratio of 1:2. The mixture is diluted to 1,000 times and has a concentration 0.001 wt %. Then the solutions are sprayed on *Terminalia boivinii* covered with aphides. The result shows that all the pests died after spraying once and then the trees grew well without pests.

The results of banana shoots and guava applied with and without the NSPs/surfactant complex of Example 5 are compared. The diluted solutions were 0.001 wt %. The result shows that the banana shoot sprayed with the solution grew obviously better. The concentrations and spraying frequencies could influence growing conditions. The result also shows that the guava sprayed with the solution grew faster, flourished leaves, bloomed and fruited more. The complex could also promote growth of vegetables such as bottle gourd.

In addition, the dilutions of the exfoliated clay/surfactant complex according to the present invention can balance acidic soil and increase utilization thereof. In the present invention, the exfoliated clay/surfactant complex is similar to a virus in size, has a large specific surface area and adsorption ability, so that viruses, bacteria and pest ova can not proceed with fissiparity or hatch because they are embedded by the complex.

The exfoliated clay/surfactant complex of the present invention are friendly to the environment and can be further used in other fields, for example, adsorbing pesticides, promoting aquaculture, treating waste water of agriculture or fishing, preserving agricultural products, deodorizing corrals or stalls, killing mosquitoes or flies, and cleaning objects or clothes.

What is claimed is:

1. A method for inhibiting plant pests, comprising a step of spraying a dispersion of an exfoliated clay/surfactant complex on a plant; wherein:
   the weight ratio of the exfoliated clay to the surfactant is 99/1 to 1/99;
   the exfoliated clay is nanosilicate platelets (NSPs); and
   the surfactant is a nonionic surfactant.
2. The method of claim 1, wherein the surfactant is polyoxyethylene alkyl ether.

3. The method of claim 1, wherein the surfactant is polyoxyethylene stearylcetyl ether.

4. The method of claim 1, wherein the exfoliated clay/surfactant complex is dispersed in water or alcohol.

\* \* \* \* \*